United States Patent [19]

Klemm

[11] Patent Number: Plant 6,997

[45] Date of Patent: Aug. 22, 1989

[54] GERANIUM PLANT NAMED MARELI

[75] Inventor: Siegfried Klemm, Stuttgart, Fed. Rep. of Germany

[73] Assignee: Klomm & Sohn, Stuttgart, Fed. Rep. of Germany

[21] Appl. No.: 237,402

[22] Filed: Aug. 29, 1988

[51] Int. Cl.[4] ..... A01H 5/02

[52] U.S. Cl. ..... Plt./68

[58] Field of Search ..... Plt./68

*Primary Examiner*—Robert E. Bagwill

*Attorney, Agent, or Firm*—Chas. W. Rummler

[57] ABSTRACT

A new and distinct variety of geranium plant particularly distinguished by the light violet color of its florets which becomes white at the center, by the very large size of its flower clusters, each of which contains about seventy well-formed florets, each floret being about 4.5 cm. in diameter and having from five to six petals; also by its abundant, dark green leaves which have no zonation and extend about 19 cm. above the soil; and by its upright, bushy growth habit, having a total height of about 30 cm.

1 Drawing Sheet

BACKGROUND OF THE NEW PLANT

My new geranium variety was originated at my nursery in Stuttgart, West Germany, in 1984, the new plant being a seedling selected from plants produced by a hybrid resulting from my crossing of the variety 'PAC-532' with the pollen parent 'PAC-614', my object being to produce a light pink, early and double blooming variety. The new plant was selected for propagation because of its most nearly meeting my breeding objective and the selected plant was asexually reproduced under my direction at Stuttgart by means of cuttings. Propagation of this plant was carried on through several succesive generations, which demonstrated conclusively that the distinctive characteristics of this new variety remain true from generation to generation and appear to be firmly fixed. At present, propagation is being done at Stuttgart by means of cuttings.

DESCRIPTION OF THE DRAWING

My new geranium variety is illustrated by the accompanying full color photographic print, which shows the form and color of the individual florets which comprise a full cluster, the color rendition being as nearly true to that herein specified as is reasonably possible to obtain by conventional photographic procedures.

DESCRIPTION OF THE NEW PLANT

The following is a detailed description of my geranium variety from observations made at Stuttgart during the Spring of 1988, the color designations being according to the The R.H.S. Colour Chart published by The Royal Horticultural Society of London, England.

THE PLANT

Origin: Seedling.

Parentage:

*Seed parent.*—'PAC 532' (unpatented).

*Pollen parent.*—'PAC-614' (unpatented).

Classification:

*Botanic.*—Pelargonium zonale hybrid.

*Commercial.*—Geranium.

Form: Bush.

Growth: Vigorous, bushy and upright with good strength and at a medium rate.

Height: About 30 to 35 cm.

Flower stem length: About 15 to 17 cm.

Branching character: Normal.

Foliage:

*Quantity.*—Abundant.

*Size of leaf.*—About 8 cm. long and 7 cm. wide.

*Leaf Shape.*—Round and closed with a crenate margin.

*Texture.*—Smooth.

*Ribs and veins.*—Four main veins on each leaf.

*Color.*—Upper side — Light to medium green, nearly no zonation. Under side — Lighter green.

THE BUD

Size: Normal.

*Diameter.*—About 0.9 cm.

*Length.*—About 12 to 14 mm.

Form: Elliptic as a pointed ovoid.

Opening rate: Medium.

Color of florets:

*When sepals first divide.*—Very Light pink.

*When petals begin to unfurl.* Light pink-violet.

Sepals:

*Number.*—Five.

*Shape.*—Linear and the sepals stand up when the flowers open.

*Color.*—Green.

Peduncle:

*Length.*—About 15 cm.

*Color.*—Green.

*Character.*—Rigid and upright.

INFLORESCENCE

Blooming habit: Continuous and profusely beginning in early Spring and continuing through midseason and Fall.

Size: A very large cluster of from 11 to 14 florets.

Florets:

*Shape.*—When bloom first opens, cup-shaped. When bloom matures, flat.

*Size.*—About 4.5 cm. in diameter.

*Petalage.*—Number of florets: 5 or 6. Arrangement: Imbricated. Form: Wide with entire margins. Texture: Soft. Appearance: Satiny. Color: Upper side — RHS 78-D. Under side — Light violet-pink.

*Petaloids.*—Number: 1 or 2. Size: About 3 to 4 mm. Color: Light violet-pink.

Flower stem:

*Length.*—About 15 cm.

*Color.*—Green.

*Character.*—Strong and upright.

Persistence: The petals stay on the flower stem about fourteen days.

REPRODUCTIVE ORGANS

Stamens:

*Number.*—Seven.

*Arrangement.*—In a ring around the pistil.

*Anthers.*—Size: About 1.5 mm. Color: Light brown.

*Filaments.*—Length: 4 mm. Color: White.

*Pollen.*—Color: Orange

Pistil:

*Number.*—One.

*Style.*—Length: About 4 mm. Color: Light green.

*Stigma.*—The stigma has five parts. Color: Frosted glas.

THE FRUIT

Fertility: The fruit is fertile.

Shape: Ovoid.

Color at maturity: Brown.

My new geranium is a completely new variety, almost simply flowering with very nice shaped flowers which have the color of faded syringa, the flowers coming very early in the Spring and also during the Summer and Fall.

I claim:

1. The new variety of geranium plant, substantially as herein shown and described and particularly distinguished by the very large size of its flower clusters and the light pink coloration of the individual florets.

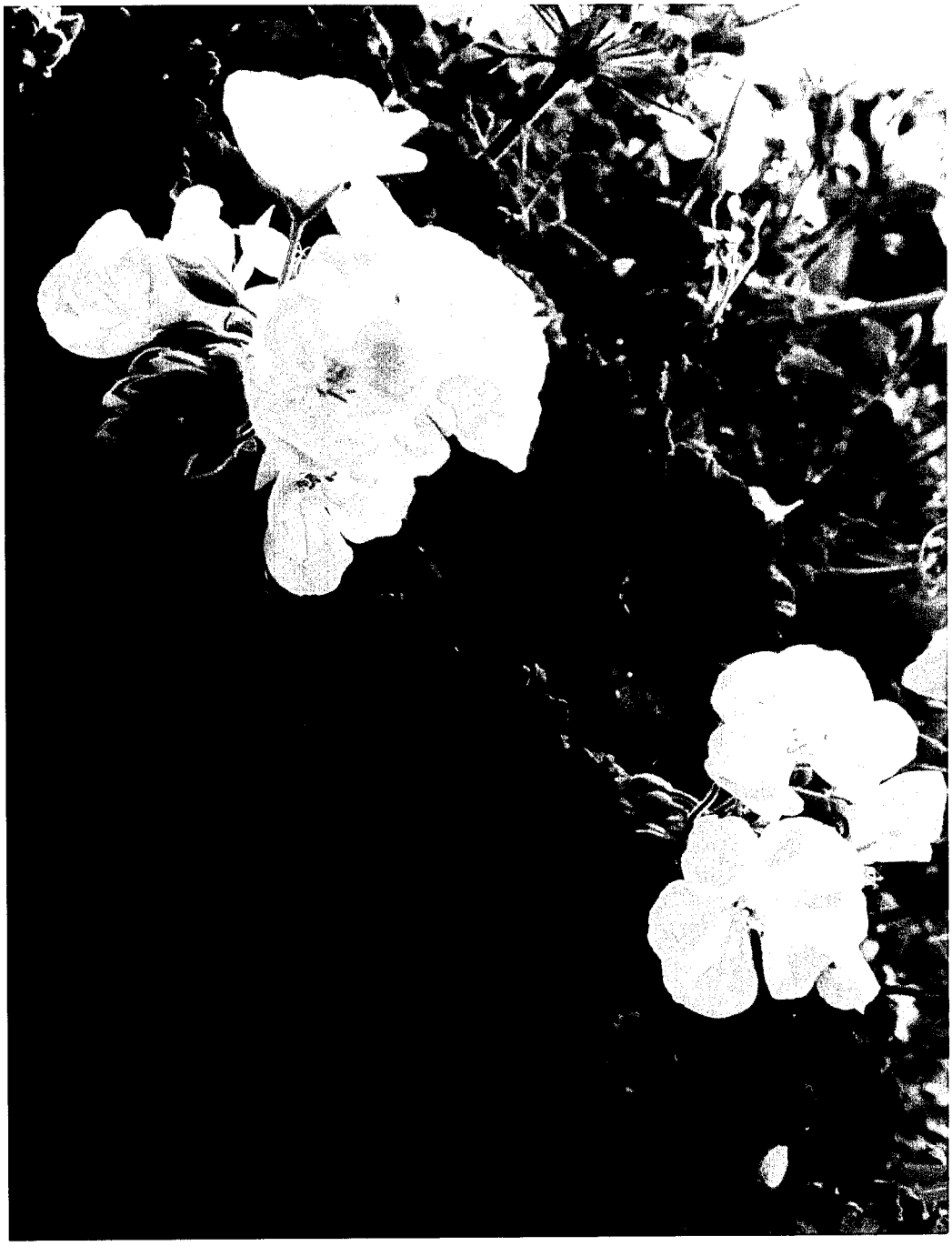

* * * * *